United States Patent [19]
Elliot

[11] Patent Number: 6,124,578
[45] Date of Patent: Sep. 26, 2000

[54] WARMER FOR FEET, NECK, AND LOWER BACK

[76] Inventor: Russell R. Elliot, 906 Lennox Rd. West, Palm Harbor, Fla. 34683

[21] Appl. No.: 09/395,617

[22] Filed: Sep. 14, 1999

[51] Int. Cl.$^7$ .................................................. H05B 3/34
[52] U.S. Cl. ........................ 219/528; 219/217; 392/443
[58] Field of Search ................... 219/201, 211, 219/212, 217, 385, 386, 522, 527, 528, 529, 532, 533, 535, 546, 549; 392/443; 5/400, 658

[56] References Cited

U.S. PATENT DOCUMENTS

| | | | |
|---|---|---|---|
| 2,032,294 | 2/1936 | McDonald | 219/528 |
| 2,498,983 | 2/1950 | D'Albora | 219/528 |
| 3,103,219 | 9/1963 | Chadner | 219/528 |
| 3,480,760 | 11/1969 | Young | 219/528 |
| 3,585,356 | 6/1971 | Hall | 219/217 |
| 3,746,835 | 7/1973 | Yu et al. | 219/217 |
| 3,790,753 | 2/1974 | Miller | 219/528 |
| 3,894,213 | 7/1975 | Agarwala | 219/528 |
| 3,982,098 | 9/1976 | Trostler | 219/217 |
| 4,044,221 | 8/1977 | Kuhn | 219/217 |
| 4,097,717 | 6/1978 | Phillips | 219/217 |
| 4,220,848 | 9/1980 | McMullan et al. | 219/528 |
| 4,233,492 | 11/1980 | McMullan et al. | 219/217 |
| 4,352,976 | 10/1982 | McMullan | 219/217 |
| 4,868,898 | 9/1989 | Seto | 219/528 |
| 4,952,776 | 8/1990 | Huguet | 219/217 |
| 5,014,399 | 5/1991 | Grisel | 5/658 |
| 5,081,339 | 1/1992 | Stine | 219/217 |
| 5,111,025 | 5/1992 | Barma et al. | 219/217 |
| 5,138,138 | 8/1992 | Theilacker et al. | 219/528 |
| 5,673,445 | 10/1997 | Suter | 5/400 |
| 5,811,760 | 9/1998 | Siebelink | 219/217 |
| 5,928,548 | 7/1999 | Johansson | 219/528 |

*Primary Examiner*—Teresa Walberg
*Assistant Examiner*—Fadi H. Dahbour
*Attorney, Agent, or Firm*—Ronald E. Smith; Smith & Hopen, P.A.

[57] ABSTRACT

A warmer for treatment of the feet, neck, and lower back area includes a frame for holding a bladder. An open-cell foam-filled cushion is disposed within the bladder and a cover having opposite ends secured to the frame overlies the bladder so that the bladder holds its shape regardless of its orientation. An opening in a top wall of the bladder allows the charging of water into the bladder. The water fills the bladder and occupies the interstitial spaces of the cushion. The frame includes a flat base that is inclined slightly relative to a horizontal support surface and that flat base supports the bladder. The foam-filled bladder conforms to the soles of feet when the warmer is used as a foot rest. When used as a pillow, the bladder conforms to a person's head and neck, and it conforms to the lower back region when the warmer is positioned in a substantially vertical orientation.

11 Claims, 4 Drawing Sheets

WARMER FOR FEET, NECK, AND LOWER BACK

BACKGROUND OF THE INVENTION

1. Field of the invention

This invention relates, generally, to therapeutic devices. More particularly, it relates to a device that warms the feet, neck and lower back of an individual and which provides relief from pain.

2. Description of the prior art

It is known that the application of a warm compress can provide relief from various physical pains. However, it is often not convenient to make a compress whenever one is needed.

The well-known hot water bottle has been used for years as a provider of relief to various discomforts as well. One of the drawbacks of a hot water bottle is that its shape changes as its position changes, thus making it unsuitable for use in some situations. Moreover, the water cools continuously after it has been charged into the bottle.

What is needed, then, is a device that provides the therapeutic benefits of a warm compress or of a hot water bottle, but which does not have the shortcomings of such devices.

More specifically, a device is needed that provides the therapeutic effects of warmth to the human foot, neck and lower back area. The device should have means for holding its shape regardless of what position it is in, and means should be provided for maintaining the temperature of the device so that it does not cool off over time.

However, it was not obvious to those of ordinary skill in this art how the needed improvements could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention. The present invention is a warmer for the feet, the neck, and the lower back area. The warmer includes a frame, a bladder of predetermined shape supported by the frame, a foam cushion having the same predetermined shape disposed within the bladder to maintain the predetermined shape of the bladder, and a flexible cover that overlies the bladder. Opposite ends of the flexible cover are secured to the frame, and the cover cooperates with the foam cushion to maintain the shape of the bladder when the bladder is placed into a plurality of differing positions.

The bladder is adapted to hold a predetermined quantity of liquid that fills the bladder and that occupies interstitial spaces of the foam cushion.

The frame includes a flat base of generally rectangular configuration. A heating pad means is disposed atop the flat base such that the heating pad means is sandwiched between the flat base and a bottom wall of the bladder when the bladder is supported by the frame.

A temperature control means is in electrical communication with said heating pad means for adjusting an amount of heat generated by the heating pad means.

It is a primary object of this invention to provide a therapeutic warmer for feet, the neck, and lower back.

Another object is to provide a warmer that provides a warmth that does not diminish over time.

Another object is to provide a warmer that holds its shape regardless of its orientation.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
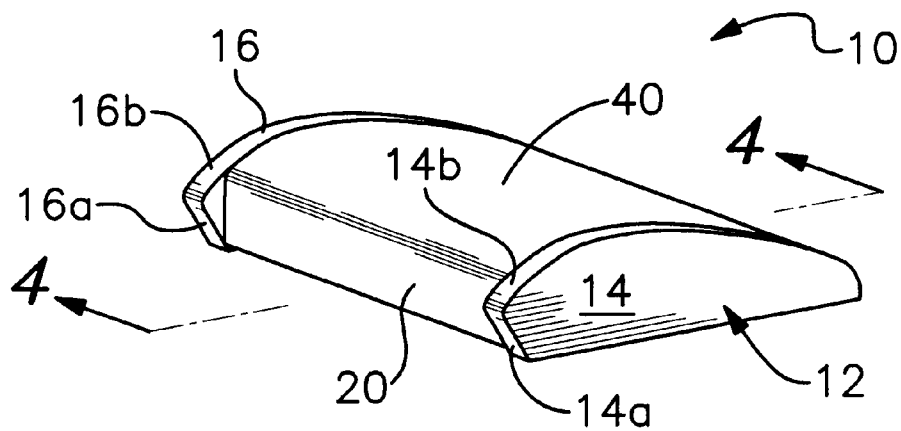
FIG. 1 is a front perspective view of the novel warmer.
Figure 2:
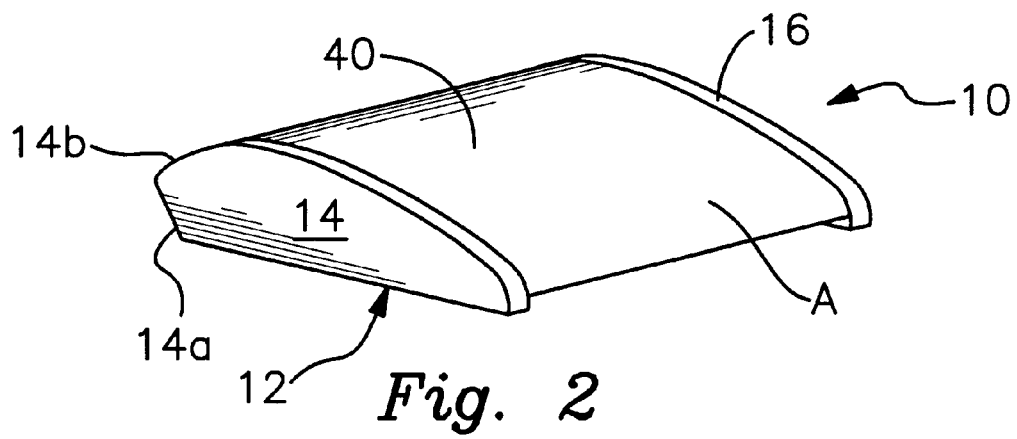
FIG. 2 is a rear perspective view thereof.
Figure 3:
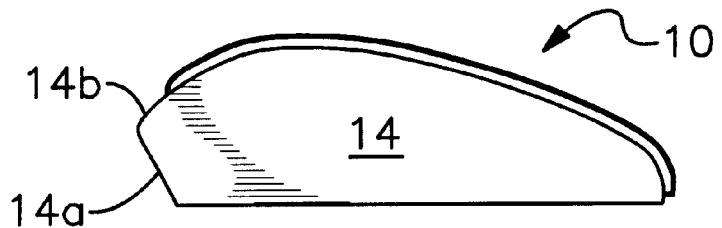
FIG. 3 is a side elevational view thereof.

Referring now to FIGS. 1–3, it will there be seen that an exemplary embodiment of the invention is denoted as a whole by the reference numeral 10.

Warmer 10, to be known commercially under the trademark WONDER WARMER foot, neck and lower back warmer, includes a frame 12 formed by a pair of parallel, flat, longitudinally disposed upstanding sidewalls 14 and 16 that are transversely spaced apart from one another.

Figure 4:
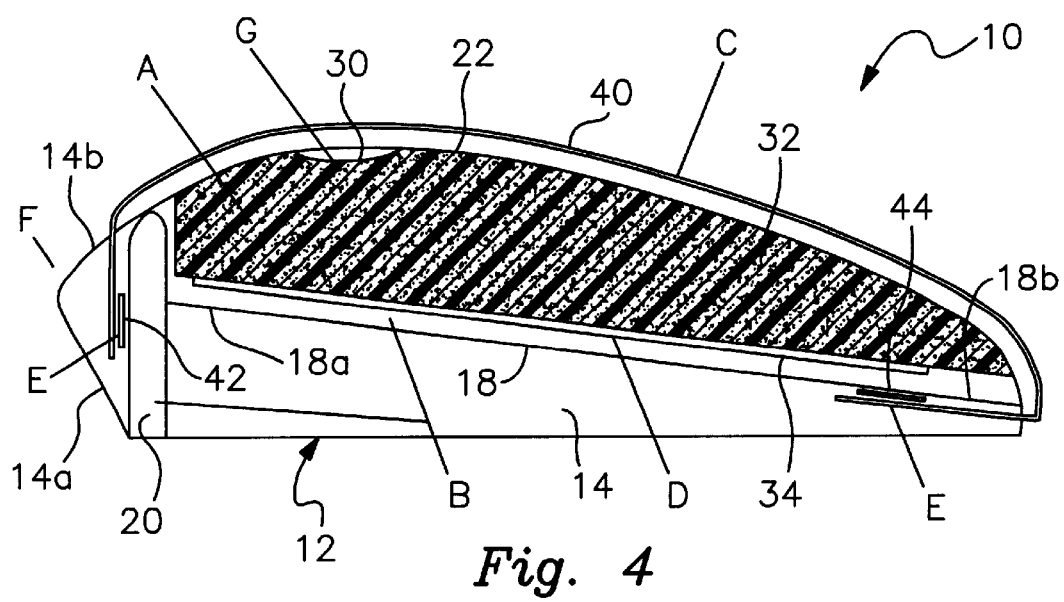
FIG. 4 is a transverse sectional view thereof, taken along line 4—4 in FIG. 1.
Figure 5:
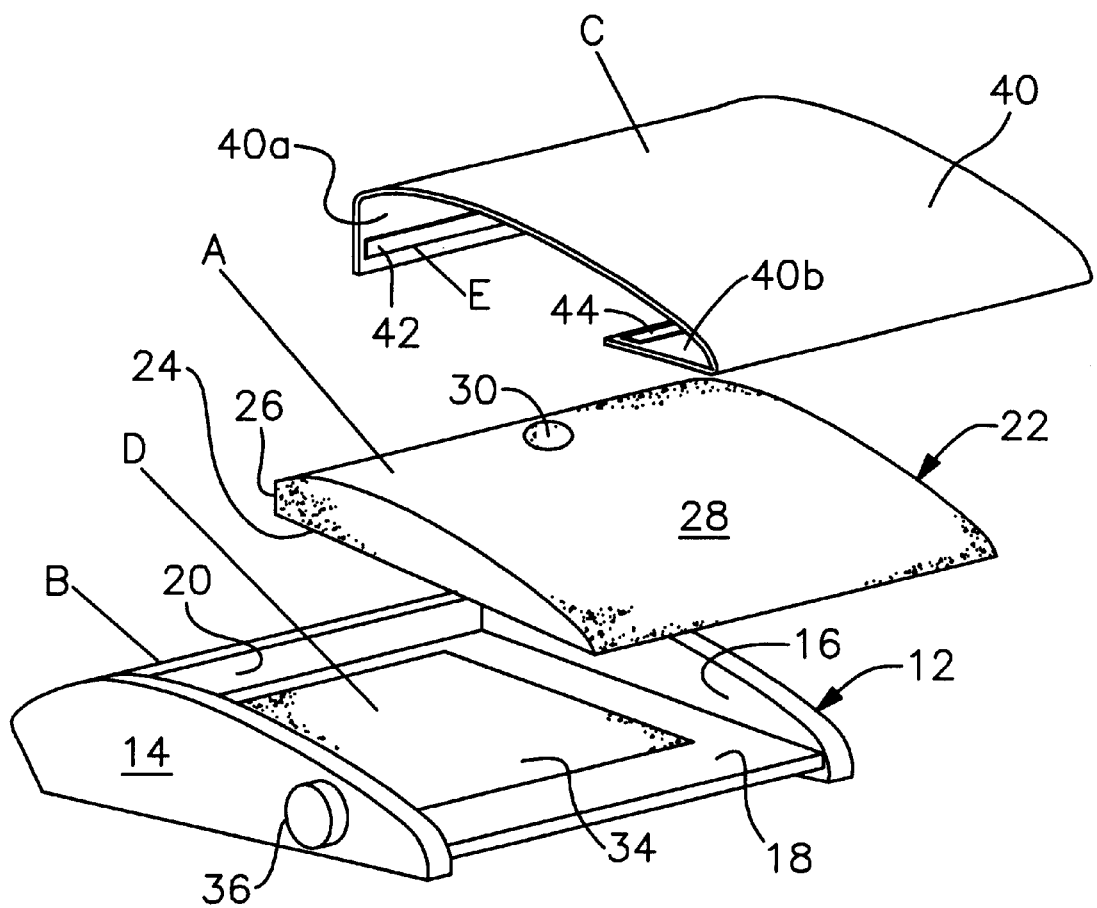
FIG. 5 is an exploded perspective view thereof.

As best understood in connection with FIGS. 4 and 5, frame 10 further includes a flat base 18 of generally rectangular configuration and a transversely disposed, upstanding forward wall 20 that interconnects the respective forward or leading ends of side walls 14, 16.

Each sidewall 14, 16 has a flat forward edge 14a, 16a that is forwardly inclined with respect to a vertical plane, and an arcuate forward edge 14b, 16b that extends rearwardly. Forwardly inclined flat edges 14a, 16a are used to support warmer 10 when it is used for low back treatment, as described hereinafter.

Flat base 18 is inclined with respect to a horizontal support surface such as a household floor, not shown, when warmer 10 is in use as a foot or neck warmer. More particularly, sidewalls 14, 16 are supported by such a support surface when warmer 10 is in such use. The transversely disposed forward or leading end 18a of flat base 18 is secured to forward wall 20 and is elevated with respect to the transversely disposed rearward or trailing end 18b of said flat base.

Bladder 22, as best understood in connection with FIG. 5, has a flat bottom wall 24, an upstanding, flat, transversely disposed forward wall 26, and a curved top wall 28 of predetermined curvature. An opening 30 is formed in top wall 28 to admit a liquid fluid such as water into bladder 28 or to drain liquid fluid therefrom. A closure means, not shown, is used to close opening 30 when warmer 10 is in use.

Bladder 22 is held into its FIG. 5 shape by a cushion 32 (FIG. 4) disposed therewithin. Cushion 32 is preferably formed of an open-cell foam such as polyurethane or the like. When water or other suitable liquid fluid is charged into opening 30, said liquid fluid fills the hollow interior of bladder 22, filling the interstitial spaces of the foam.

Heating pad 34, depicted in FIGS. 4 and 5, is positioned in overlying relation to flat base 18. Accordingly, it is sandwiched between said flat base 18 and bottom wall 24 of bladder 22 when bladder 22 is positioned within frame 12. A rotatably mounted temperature control means, preferably in the form of knob 36, is mounted on sidewall 14 or any other suitable location and is in electrical communication with heating pad 34. Rotation of control knob 36 in a first direction lowers the current to heating pad 34 and rotation of said knob in a second direction increases said current. In this way, the user controls the temperature of the liquid fluid within bladder 22. A thermostat means, not shown, maintains the selected temperature within a predetermined range so that the liquid fluid does not cool down over time.

Cover 40, preferably formed of a fabric, aesthetically covers bladder 22 and works in combination with cushion 32 to maintain the shape of the bladder, especially when the bladder is placed in a generally vertical orientation as described below. An elongate, transversely disposed strip of a hook and loop fastening means 42 is secured to the underside of leading end 40a thereof, and a similar strip 44 is secured to the underside of trailing end 40b thereof. As depicted in FIG. 4, strip 42 is releasably engaged to a mating strip of hook and loop material, not shown, that is secured to forward wall 20 of frame 12. Strip 44 is releasably engaged to a mating strip of hook and loop material, not shown, that is secured to an underside of flat base 18 near its trailing end.

Figure 6:
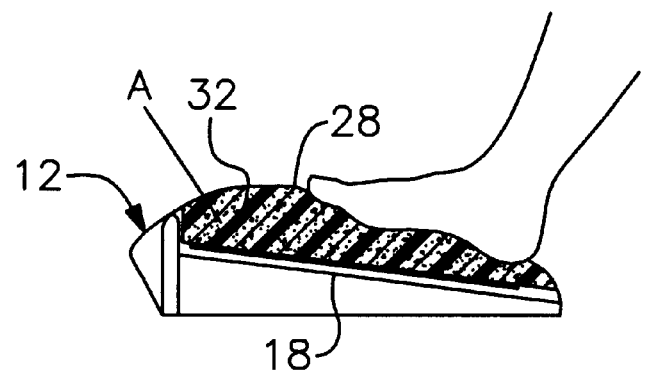
FIG. 6 is a side elevational view depicting the novel warmer when used to provide therapeutic warmth to feet.

As indicated in FIG. 6, the inherent bias of cushion 32 causes it to conform to the contour of the soles of a foot or feet placed atop bladder 22. Moreover, the inclination of flat base 18 and the predetermined arcuate curvature of top wall 28 of said cushion combine to position the heel of the foot at an elevation lower than the toes thereof, flexing the ankle in a therapeutically beneficial way.

Figure 7:
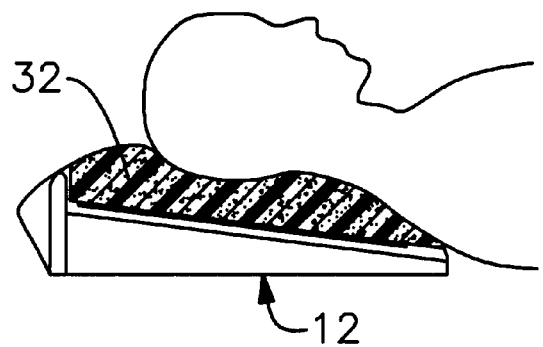
FIG. 7 is a side elevational view depicting the novel warmer when used to provide therapeutic warmth to a neck.

FIG. 7 shows the novel structure in use for neck treatment. Again, the inherent bias of foam cushion 32 enables it to conform to the curvature of the head and neck. Note that frame 12 has no back wall to interfere with the shoulders of the reclining person.

Figure 8:
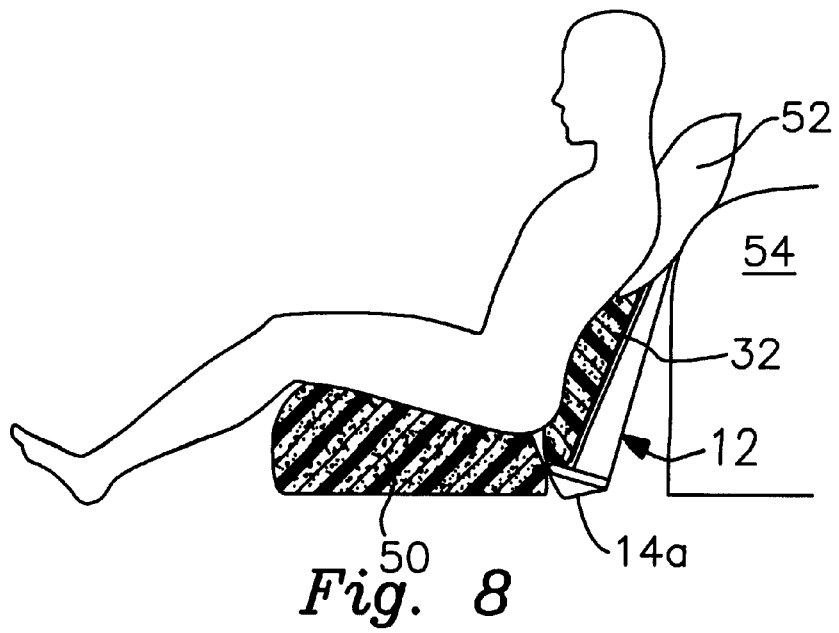
FIG. 8 is a side elevational view depicting the novel warmer when used to provide therapeutic warmth to a lower back area.

FIG. 8 depicts warmer 10 when in use for lower back pain treatment. When in such use, frame 12 is placed in a substantially vertical position, with the above-mentioned forward edges 14a, 16a of sidewalls 14, 16, respectively, being in overlying relation to a support surface such as a household floor. The inherent bias of foam cushion 32 and the extra support provided by cover 40 helps maintains the shape of bladder 22 and enables the bladder to conform to the shape of the person's lower back area. The combination of foam cushion 32 and cover 40 prevents the water or other liquid fluid within said bladder from falling to the bottom of the bladder and distorting its shape. In other words, foam cushion 32 and cover 40 maintain the shape of bladder 22 regardless of the orientation of bladder 22.

When warmer 10 is in use in the manner depicted in FIG. 8, it is advantageous to further employ a wedge-shaped cushion 50, which may be foam-filled but not liquid filled, as the means for supporting the person's weight. A pillow 52 may also be used to support the shoulders. Note that warmer 10 is supported from behind by a common heavy item of furniture such as a chair or a sofa 54.

Patients suffering from lower back pain, unable to find relief from surgical or chiropractic treatment, have reported relief from such pain after use of the novel warmer of this invention for a predetermined amount of time, such as twenty minutes. Similar successes have been reported in connection with foot and neck pain.

The thermostat means of this invention is set to prevent water temperature from exceeding a predetermined threshold, such as 102°, for example.

Frame 12 may be made of any suitable material, such as wood or high impact plastic.

This invention represents a major breakthrough in the art of therapeutic warmers. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A warmer for feet, the neck, and lower back area, comprising:

a frame;

a bladder supported by said frame;

said bladder having a predetermined shape;

an open-celled foam cushion having interstitial spaces disposed within said bladder, said foam cushion having substantially the same predetermined size and shape of said bladder;

said bladder holding a predetermined quantity of liquid;

said predetermined quantity of liquid filling said bladder and occupying said interstitial spaces of said open-celled foam cushion;

said open-celled foam cushion having an inherent bias that maintains its own shape and said predetermined shape of said bladder as well when said bladder is positioned in differing orientations, a flexible cover disposed in overlying relation to said bladder;

said flexible cover being secured at opposite ends to said frame to secure said bladder to said frame;

said cover cooperating with said open-celled foam cushion to maintain said predetermined shape of said bladder when said bladder is placed into said differing preselected orientations.

2. The warmer of claim 1, wherein said frame includes a flat base of generally rectangular configuration, a pair of longitudinally disposed, parallel sidewalls mounted at opposite ends of said base, and a transversely disposed front wall mounted at a forward end of said flat base whereby a transversely disposed rearward end of said frame is open.

3. The warmer of claim 2, wherein said flat base is mounted on an incline relative to a horizontal support surface such that a forward transversely disposed edge of said flat base is elevated with respect to a rearward transversely disposed edge thereof.

4. The warmer of claim 3, wherein said predetermined shape of said open celled foam cushion includes a flat bottom wall of generally rectangular configuration, a pair of flat, transversely spaced apart, longitudinally disposed sidewalls, a flat, transversely disposed forward wall, a transversely disposed rearward edge, and a curved top wall of predetermined curvature that extends from an uppermost edge of said forward wall to said rearward edge.

5. The warmer of claim 4, wherein said predetermined shape of said bladder includes a flat bladder bottom wall of generally rectangular configuration, a pair of flat, transversely spaced apart, longitudinally disposed bladder sidewalls, a flat, transversely disposed bladder forward wall, a transversely disposed bladder rearward edge, and a curved bladder top wall of predetermined curvature that extends from an uppermost edge of said bladder forward wall to said bladder rearward edge.

6. The warmer of claim 5, further comprising a heating pad means disposed atop said flat base, said heating pad means being sandwiched between said flat base and said flat bladder bottom wall when said bladder is supported by said frame.

7. The warmer of claim 6, further comprising temperature control means in electrical communication with said heating pad means for adjusting an amount of heat generated by said heating pad means.

8. The warmer of claim 7, further comprising means for releasably attaching a forward end of said flexible cover to said frame front wall and means for releasably attaching a rearward end of said flexible cover to an underside of said flat base of said frame.

9. The warmer of claim 8, wherein a transversely disposed strip of hook and loop fastening means is secured to said front wall of said frame and wherein a complementary strip of hook and loop fastening means is secured to an underside of said flexible cover along said forward end so that said forward end of said flexible cover is releasably attachable to said front wall of said frame.

10. The warmer of claim 9, wherein a transversely disposed strip of hook and loop fastening means is secured to an underside of said flat base of said frame near a rearward end of said flat base and wherein a complementary strip of hook and loop fastener means is secured to an underside of said flexible cover near said rearward end so that said rearward end of said flexible cover is releasably attachable to said underside of said flat base.

11. The warmer of claim 10, further comprising an opening formed in said top wall of said bladder, said opening adapted to receive a closure means for closing said opening so that said liquid can be added to and withdrawn from said bladder.

* * * * *